United States Patent [19]
Jacklin et al.

[11] Patent Number: 5,124,166
[45] Date of Patent: Jun. 23, 1992

[54] CARBOXY/CARBOXYLATE DISUBSTITUTED ESTERS AS EDIBLE FAT MIMETICS

[75] Inventors: Peter T. Jacklin, Waldwick, N.J.; Ronald P. D'Amelia, Hicksville, N.Y.; Lawrence P. Klemann, Somerville; John W. Finley, Whippany, both of N.J.

[73] Assignee: Nabisco, Inc., Parsippany, N.J.

[21] Appl. No.: 527,066

[22] Filed: May 21, 1990

Related U.S. Application Data

[63] Continuation-in-part of Ser. No. 439,103, Nov. 18, 1989, which is a continuation-in-part of Ser. No. 231,393, Aug. 12, 1988, abandoned, which is a continuation-in-part of Ser. No. 85,434, Aug. 13, 1987, Pat. No. 4,830,787.

[51] Int. Cl.$^5$ ............................ A23L 1/29; C09F 5/00
[52] U.S. Cl. .................................. 426/531; 426/496; 426/601; 426/611; 426/804; 554/223; 554/224; 554/227
[58] Field of Search ............... 426/531, 601, 603, 607, 426/611, 613, 804, 496; 260/410, 410.9 R

[56] References Cited

U.S. PATENT DOCUMENTS

| | | |
|---|---|---|
| 519,980 | 5/1894 | Winter . |
| 2,789,992 | 4/1957 | Thompson et al. ............. 260/410.9 |
| 2,924,528 | 2/1960 | Barsky et al. .................... 99/118 |
| 2,962,419 | 11/1960 | Minich ............................ 167/81 |
| 2,993,063 | 7/1961 | Alsop et al. .................... 260/410.6 |
| 3,208,857 | 9/1965 | Howard et al. .................. 99/123 |
| 3,244,534 | 4/1966 | Buddemeyer et al. .......... 99/91 |
| 3,495,010 | 2/1970 | Fossel ............................ 424/312 |
| 3,526,518 | 9/1970 | Kleiman ......................... 426/308 |
| 3,579,548 | 5/1971 | Whyte ............................ 260/410.7 |
| 3,600,186 | 8/1971 | Mattson et al. ................. 99/1 |
| 3,637,774 | 1/1972 | Babayan et al. ................ 260/410.6 |
| 3,876,794 | 4/1975 | Rennhard ....................... 426/152 |
| 3,954,976 | 5/1976 | Mattson et al. ................. 424/180 |
| 4,005,195 | 1/1977 | Jandacek ....................... 424/180 |
| 4,034,083 | 9/1977 | Mattson ........................ 424/180 |
| 4,304,768 | 12/1981 | Staub et al. .................... 424/180 |
| 4,482,927 | 11/1984 | Melbye et al. ................. 360/40 |
| 4,508,746 | 4/1985 | Hamm ........................... 426/601 |
| 4,582,927 | 7/1986 | Fulcher ......................... 560/201 |
| 4,797,300 | 1/1989 | Jandacek et al. .............. 426/549 |
| 4,830,787 | 5/1989 | Klemann et al. .............. 426/611 |
| 4,840,815 | 6/1989 | Meyer et al. .................. 426/611 |
| 4,849,242 | 7/1989 | Kershner ...................... 426/601 |
| 4,861,613 | 8/1989 | White et al. ................... 426/611 |
| 4,915,074 | 4/1990 | D'Amelia et al. ............. 426/611 |

FOREIGN PATENT DOCUMENTS

| | | |
|---|---|---|
| 1106681 | 11/1978 | Canada . |
| 34858 | 9/1981 | European Pat. Off. . |
| 184259 | 11/1985 | European Pat. Off. . |
| 205273 | 5/1986 | European Pat. Off. . |
| 233856 | 2/1987 | European Pat. Off. . |
| 236288 | 9/1987 | European Pat. Off. . |
| 1815706 | 3/1968 | Fed. Rep. of Germany . |
| 2456631 | 5/1974 | Fed. Rep. of Germany . |
| 3529564 | 8/1985 | Fed. Rep. of Germany . |
| 952849 | 1/1967 | United Kingdom . |

OTHER PUBLICATIONS

Chemical Abstracts RN7492-70-8, 1990.
Fallat, R. W., et al., Am. J. Clin. Nutrition, 29: 1204–1215 (1976).
Booth, A. N., and Gros, A. T., 40 *J Amer. Oil Chem Soc.* 551–553 (1963).
Feuge, R. O., and Ward, T. L., 80 *J. Amer. Chem. Soc.* 6338–6341 (1958).
Feuge, R. O., et al. 37 *J. Amer. Oil Chem. Soc.* 291–294 (1960).
Goodman and Gilman's *Pharmacological Basis of Therapeutics*, 7th ed., Macmillan Publishing Co., New York, 1002–1003 (1985).
Gottenbos, J. J., Chap. 8 in Beace-Rogers, J., ed., *Dietary Fat Requirements in Health and Development.* A.O.C.S., 109 (1988).
Hamm, D. J., 49 Journal of Food Science, 419–428 (1984).
Haumann, B. J., 63 J. Amer. Oil Chem. Soc. 278–288 (1986).
Hess, K., and Messmer, E., 54 Ber. 499–523 (1921). [full German text and translation].
La Barge, R. G., 42 Food Tech. 84–90 (1988).
Mead, J., et al., *Lipids,* Plenum, NY, 459–470 (1986).
Nikkari, T., and Haahti, E., 164 Biochim. Biophys. Acta 294–305 (1968).
Ponomareff-Baumann, M., et al., 43 Pharm. Acta Helv. 158–176 (1968). [full German text and translation].
Shull, R. L., et al., 38 J. Amer. Chem. Soc., 84–86 (1961).
Stryker, W. A., 31 Arch. Path 670–692 (1941).
Ward, T. L., et al., J. Amer. Oil Chem. Soc. 667–671 (1951).

*Primary Examiner*—Joseph Golian
*Assistant Examiner*—Evan Federman
*Attorney, Agent, or Firm*—Stephen B. Shear

[57] ABSTRACT

Novel fat mimetic compounds and their uses in food compositions are disclosed. These compounds comprise a backbone to which is attached one hydroxyl group acylated with a fatty acid, forming a pendant carboxy substituent ($—O_2C—R'$, where R' is an aliphatic group having 1 to 30 carbons), and one carboxylic acid group esterified with a fatty alcohol, forming a pendant carboxylate substituent ($—CO_2R'$, with R' as defined above).

20 Claims, No Drawings

CARBOXY/CARBOXYLATE DISUBSTITUTED ESTERS AS EDIBLE FAT MIMETICS

RELATED APPLICATIONS

This application is a continuation-in-part of copending application Ser. No. 07/439,103, filed Nov. 18, 1989, which was a continuation-in-part of serial number 07/231,393, filed Aug. 12, 1988, which, in turn, was a continuation-in-part of U.S. Ser. No. 07/085,434, filed Aug. 13, 1987.

BACKGROUND OF THE INVENTION

The present invention relates to new fat mimetic compounds and their uses in edible compositions. These compounds comprise a backbone to which is attached one fatty —$CO_2R'$ (carboxylate) group and one fatty —$O_2C$—$R'$ (carboxy) group. In one embodiment, carboxy/carboxylate disubstituted esters are partially digestible.

Obesity is perceived as a common problem in contemporary society. This condition is due, in many people, to a greater intake of calories than are expended. While genetic and behavioral factors play a major role, it is generally agreed that reasonable modifications of the caloric value of foods can be valuable in reaching a desirable equilibrium weight for an individual predisposed to obesity.

Many foods which provide gustatory satisfaction contain significant fat levels. This can be a problem for individuals drawn to these foods because fat has about twice the caloric density of protein and carbohydrates. It has, in fact, been estimated that fat contributes about 40% of the total calories in the diet. It has long been desired to reduce the available calories of dietary fat without decreasing the appeal or satiety expected of fatty foods. It has been reported that this would offer a convenient and practical method by which obesity could be controlled, ideally without requiring a dieter to restrict total food intake.

A reduction in fat content has been suggested for other reasons as well. Certain fats appear to pose a health risk when consumed in large quantities over time. Moreover, the amount of fat in the American diet has increased in the last 60 years by about 25% (Mead, J., et al *Lipids*, Plenum, N.Y., 1986, page 459). A number of national advisory committees on nutrition have presented their findings which differ in detail, but share as a common point the recommendation of reducing the total amount of fat in our diet (Gottenbos, J.J., chapter 8 in Beare-Rogers, J., ed., *Dietary Fat Requirements in Health and Development*, A.O.C.S. 1988, page 109). Hence, major research efforts have focused on ways to produce food substances that provide the same functional and organoleptic properties as fats, but not the calories.

A number of fat replacements have heretofore been suggested (recently reviewed by Hamm, D.J., 49 *J. Food Sci.* 419–428 (1984), Haumann, B.J., 63 *J. Amer. Oil Chem. Soc.* 278–288 (1986) and LaBarge, R.G., 42 *Food Tech.* 84–90 (1988). Hamm divides replacement fats into two broad categories: structurally re-engineered triglycerides modified to retain their conventional functional properties in foods, while removing their susceptibility toward hydrolysis or subsequent absorption during digestion, and materials developed from chemistry unrelated to triglycerides.

Examples of the former class of triglyceride analogues include compounds having the glycerol moiety replaced with alternate polyols (e.g., pentaerythritol in U.S. Pat. No. 2,962,419 to Minich, or sugars, suggested by Hess, K., and Messmer, E., 54B *Ber.* 499–523 (1921), and patented years later by Mattson and Volpenhein, U.S. Pat. No. 3,600,186, and Meyer, et al., U.S. Pat. No. 4,840,815); compounds having the fatty acids replaced with alternate acids (e.g., branched esters as described in U.S. Pat. No. 3,579,548 to Whyte); compounds having insertions between the glycerol and the fatty acid (e.g., ethoxy or propoxy groups in U.S. Pat. No. 4,861,613 to White and Pollard); compounds having reversed esters (e.g., malonates in U.S. Pat. No. 4,482,927 to Fulcher and trialkoxytricarballylates in U.S. Pat. No. 4,508,746 to Hamm); and compounds having the ester bonds replaced by ether bonds (Can. Pat. No. 1,106,681 to Trost).

Related to triglyceride analogues are dimeric fat replacements. Thirty years ago, the U.S.D.A. assessed the caloric availability and digestibility of a series of new-type fats, including dibasic acid-bridged diglycerides (specifically, fumaric, succinic and adipic-bridged diglyceride esters; see Feuge, R.O., and Ward, T.L., 80 *J. Amer. Chem. Soc.* 6338–6341 (1958); Ward, T.L., et al. 36 *J. Amer. Oil Chem. Soc.* 667–671 (1959); Feuge, R.O., and Ward, T.L., 37 *J. Amer. Oil Chem. Soc.* 291–294 (1960); and Shull, R.L., et al. 38 *J. Amer. Oil Chem. Soc.* 84–86 (1961)). Minich suggested ether-bridged dipentaerythritol esters about the same time (U.S. Pat. No. 2,962,419, column 53 to 76), although he exemplified only pentaerythritol ester monomers.

Examples of Hamm's second category of fat replacements chemically unrelated to triglycerides are mineral oil (suggested as early as 1894 in U.S. Pat. No. 519,980 to Winter); polyglucose and polymaltose (U.S. Pat. No. 3,876,794 to Rennhard); jojoba wax (W. Ger. Pat. No. 3,529,564 to Anika); polyoxyalkylene esters (U.S. Pat. No. 4,849,242 to Kershner); polyvinyl alcohol esters (U.S. Pat. No. 4,915,074 to D'Amelia and Jacklin); and polysiloxane (Eur. Pat. Ap. No. 205,273 to Frye).

Nondigestible or nonabsorbable edible fat replacements have proved disappointing when tested in feeding trials, where gastrointestinal side effects occurred, in some cases so extreme that frank anal leakage was observed. Nondigestible fats appear to act as a laxative and are expelled from the body, eliciting foreign body reactions like those early documented for mineral oil (Stryker, W.A., 31 *Arch. Path.* 670–692 (1941), more recently summarized in Goodman and Gilman's *Pharmacological Basis of Therapeutics*, 7th ed., Macmillan Pub. Co., N.Y. 1985, pp. 1002–1003). Similarly, experimental fats synthesized by the U.S.D.A group mentioned above exhibited undesirable gastrointestinal side effects when the compounds were fed to rats (Booth, A.N., and Gros, A.T., 40 *J. Amer. Oil Chem. Soc.* 551–553 (1963)); in several of the balance studies, the diarrhea was so extreme that digestibility coefficients could not be calculated (*ibid.*, Table I, p. 552).

Polyglycerol and polyglycerol esters, suggested as fat replacements by Babayan and Lehman (U.S. Pat. No. 3,637,774), have been suggested for use as fecal softening agents as well (U.S. Pat. No. 3,495,010 to Fossel). A number of remedies have been recommended to combat the anal leakage observed when sucrose polyesters are ingested (e.g., employing cocoa butters, U.S. Pat. No. 4,005,195 to Jandacek, incorporating saturated fatty groups, Eur. Pat. Ap. No. 233,856 to Bernhardt, or mixing residues, U.S. Pat. No. 4,797,300 to Jandacek, et al.), and dietary fiber preparations have been incorporated into polysaccharide and/or polyol-containing foodstuffs to help inhibit the diarrheal effect (U.S. Pat. No. 4,304,768 to Staub et al.). Partially digestible fat replacements have also been suggested (U.S. Pat. No. 4,830,787 to Klemann and Finley, which is fully incorporated herein by reference, and U.S. Pat. No. 4,849,242, cited above).

SUMMARY OF THE INVENTION

An object of the present invention is to provide a new class of fat mimetic compounds, methods of using them in edible compositions, and food compositions which contain them. More particularly, it is an object of the present invention to suggest carboxy/carboxylate disubstituted ester edible fat mimetics, compounds substituted with one fatty carboxylate group and with one fatty carboxy group.

The compounds of this invention may be defined by the following formula:

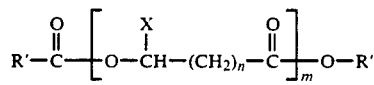

where
m = 1 to 20,
n = 0 to 12,
X = H, or an alkyl group having 1 to 16 carbon atoms, and
R' is an aliphatic group having 1 to 30 carbon atoms, the various R' groups being the same or different.

The fat mimetics of this invention comprise compounds having a backbone bearing a pendant hydroxyl group acylated with a fatty acid, forming a carboxy substituent ($-O_2C-R'$, where R' is an aliphatic group having 1 to 30 carbons), and a pendant carboxylic acid group esterified with a fatty alcohol, forming a carboxylate substituent ($-CO_2R'$, with R' as defined above).

The compounds are employed in any edible composition or any food preparation process where a fat or oil is normally employed, in total or partial replacement.

DETAILED DESCRIPTION OF THE INVENTION

Propylene glycol diesters have been suggested as fat replacements for cocoa butter (U.S. Pat. No. 2,924,528 to Barsky, et al., and U.S. Pat. No. 2,993,063 to Alsop and Carr). Enzymatic hydrolysis by lipase in a synthetic gastric juice was subsequently shown to be somewhat slower for myristic, palmitic and stearic full esters of a similar diol, ethylene glycol, than for the corresponding triglyceride counterparts (Ponomareff-Baumann, M., et al. 43 *Pharm. Acta Helv.* 158–176 (1968)). However, like diglycerides, these compounds have two hydroxyl groups acylated with fatty acids.

The compounds of this invention, in contrast, have one hydroxyl group acylated with a fatty acid and one carboxylic acid group esterified with a fatty alcohol. Thus, as compared to diglycerides having two conventional esters, the compounds of this invention have one conventional ester and one reversed ester.

The fat mimetics of this invention can be defined by the following formula:

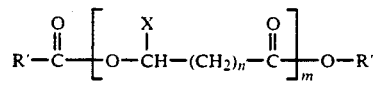

where
m = 1 to 20,
n = 0 to 12,
X = H, or an alkyl group having 1 to 16 carbon atoms, and
R' is an aliphatic group having 1 to 30 carbon atoms, the various R' groups being the same or different.

The new class of compounds, called carboxy/carboxylate disubstituted ester fat mimetics, have groups defined with reference to their connection to a backbone. Carboxylates have carbons attached to the backbone; carboxy groups have ester oxygen attached to the backbone.

The fat mimetic compounds of this invention may comprise compounds having a backbone derived from any hydroxycarboxylic acid having 2 to 20 carbons known to those skilled in the art, including, but not limited to, glycolic acid ($CH_2OH-COOH$), lactic acid (also called 2-hydroxypropanoic, $CH_3-CHOH-COOH$), hydracrylic acid (also called 3-hydroxypropanoic acid, ($CHOH-CH_2COOH$), hydroxybutanoic acid (either 2-hydroxybutanoic, $CH_3CH_2-CHOH-COOH$; 3-hydroxybutanoic, $CH_3-CHOH-CH_2-COOH$; or 4-hydroxybutanoic, $CHOH-(CH_2)_2-COOH$), hydroxypentanoic acid (either 2-hydroxypentanoic, $CH_3-(CH_2)_2-CHOH-COOH$; 3-hydroxy pentanoic, $CH_3-(CH_2)_2-CHOH-CH_2-COOH$; 4-hydroxypentanoic, $CH_3-CHOH-(CH_2)2-COOH$; or 5-hydroxypentanoic, $CHOH-(CH_2)_3COOH$), and the like acids. Longer backbones may be derived from 12-hydroxystearic and the like acids. Chemical formulae include isomeric variations. Where the backbones are prepared from mixtures of hydroxycarboxylic acids, the X's and n's in the above formula will differ depending on the acids employed.

The acylated hydroxyl group and esterified carboxylate group may be positioned anywhere, vicinally or distally, on a $C_2$ to $C_{20}$ backbone. Thus, the compounds of this invention encompass long chain acylated hydroxycarboxylic esters having carboxy and carboxylate substituents separated by a stretch of backbone as in the case, for example, of a fatty acid acylated 12-hydroxy-dedecanoic acid ester, and those having proximal carboxy and carboxylate substituents, as in the case of an otherwise structurally similar acylated 2-hydroxy-dodecanoic acid ester.

The fat mimetic compounds of this invention further encompass, as backbones, dimers, trimers, tetramers, pentamers, and other oligomers of hydroxycarboxylic acids, which bear one hydroxyl group that can be acylated an one carboxylate group that can be esterified. For example, lactic acid oligomers such as lactyl lactate ($CH_3-CHOH-(CO)-O-CH(CH_3)-COOH$), dilactyl lactate ($CH_3-CHOH-(CO)-O-CH(CH_3)-(CO)-O-CH(CH_3)-COOH$), or higher oligomers having an hydroxyl group acylated with a fatty acid, forming a pendant carboxy substituent ($-O_2C-R'$, where R' is an aliphatic group having 1 to 30 carbons), and a carboxylic acid group esterified with a fatty alcohol, forming a pendant carboxylate substituent ($-CO_2R'$, with R' as defined above), are encompassed by this invention. This invention also encompasses, as backbones, condensation products of mixed hydroxycarboxylic acids.

Thus, this invention encompasses acylated lactic acid esters of the formula

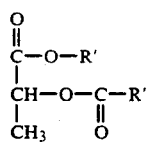

acylated lactic acid lactate esters of the formula

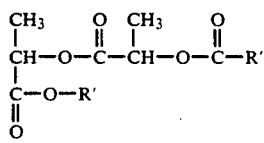

acylated lactyl lactic acid lactate esters of the formula

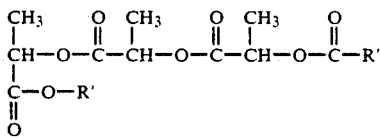

where R' is an aliphatic group having 1 to 30 carbons, and the like.

The R' groups are analogous to fatty acid residues of natural triglyceride fat and are selected from among aliphatic groups effective to form fat mimetic materials having a perceptible fat-like character. R' may be straight or branched, saturated or unsaturated, and typically are derived from fatty alcohols or fatty acids.

The R' group attached as a carboxy may be formed by acylating an hydroxyl attached to the backbone starting material with a fatty acid of the formula R'COOH, or a fatty acid derivative. Examples of fatty acids are acetic, propionic, butyric, caproic, caprylic, pelargonic, capric, undecanoic, lauric, myristic, palmitic, stearic, arachidic, behenic, lignoceric, cerotic, montanic, melissic, palmitoleic, oleic, vaccenic, linoleic, linolenic, eleostearic, arachidonic, erucic, brassidic, nervonic, eicosapentaenoic, docosatetraenoic, docosapentaenoic, docosahexaenoic, and the like acids.

Mixtures of fatty acids may also be used, for example, those derived from the hydrolysis of natural oils such as soybean, safflower, sunflower, sesame, peanut, corn, olive, rice bran, canola, babassu nut, coconut, palm, palm kernel, lupin, nasturtium seed, mustard seed, cottonseed, low erucic rapeseed or marine oils, or partially hydrogenated or fully hydrogenated oils. Fatty acids derived from other fats such as milk butterfat, lard or tallow, or plant waxes such as jojoba, may also be used. Specific fractions of natural or processed oils or waxes may also be used.

The R' group attached as a carboxylate may be formed by esterifying a carboxylic acid group attached to the backbone starting material with a fatty alcohol of the formula R'CH$_2$OH. Examples of fatty alcohols are of a similar chain length and configuration as the fatty acids enumerated above, namely, ethyl, propyl, butyl, hexyl, caprylyl, pelargonyl, capryl, lauryl, undecanyl, myristyl, palmityl, stearyl, arachidyl, erucyl, brassidyl, behenyl, lignoceryl, cerotyl, montanyl, melissyl, palmitoleyl, oleyl, vaccenyl, linoleyl, linolenyl, eleostearyl, arachidyl, nervonyl, eicosapaentanyl, docosatetraenoyl, docosapentaenyl, docosahexaenyl, and the like alcohols. Mixtures of fatty alcohols may also be used, such as those obtained from the natural or processed oils, fats or waxes listed above.

The R' groups are generally added sequentially. Thus, acylated hydroxycarboxylic acid esters of this invention may be prepared by esterifying the corresponding hydroxy acid with a fatty alcohol, and then acylating the ester thereby produced with a fatty acid, a fatty acid chloride or a fatty acid anhydride. Alternatively, the hydroxy acid may be first acylated with a fatty acid or fatty acid derivative mentioned above, and then esterified. Likewise, the acylated oligomeric hydroxy carboxylic acids of this invention may be prepared by condensing the corresponding hydroxy acid to form an oligomer, and then esterifying and acylating or acylating and esterifying the oligomeric acid as described above. Example syntheses are set out in the next section.

Having both the hydroxyl group acylated and the carboxylic acid group esterified distinguishes the compounds of this invention from acyl polylactic acid and the like emulsifiers (U.S. Pat. No. 2,789,992 to Thompson and Buddemeyer and U.S. Pat. No. 3,244,534 to Buddemeyer Moneymaker and Meyer), high molecular weight carboxylic acid esters, condensation products of hydroxy compounds and carboxylic acids, and the like surface-active agents for food compositions (U.S. Pat. No. 3,208,857 to Howard and Koren).

Moreover, since the compounds of this invention serve functionally as fat mimetics, the R, groups are selected to provide a discernible fatty character in the compounds, in contrast to an emulsifying character such as that described for the above surfactants, or a waxy character such as that described for the 2-hydroxy fatty acid diester rat skin lipids of Nikkari, T., and Haahti, E., 164 Biochim. Biophys. Acta, 294–305 (1968). Thus, many of the R' groups may have 4 or more carbon atoms, with a percentage containing 4 to 23 carbon atoms, more narrowly 10 to 20, and even more narrowly, 14 to 18 carbon atoms. In the case of carboxy groups, at least 95% of the R' groups may contain 13 to 17 carbon atoms (derived from acids having 14 to 18 carbons), with at least 80% containing 17 carbon atoms. In the case of carboxylate functionalities, at least 95% of the R' groups may contain 16 to 18 carbon atoms, with at least 80% containing 18 carbons.

In one embodiment, carboxy and carboxylate groups attached to the backbone offer differential reactivity with respect to cleavage by digestive enzymes. This results not only in the controlled and limited availability of effective caloric value, but also the selective conversion of the fat mimetic to a product or intermediate with a less oil-like nature. The more readily digestible carboxylic acid residue (i.e., the carboxy function) can be a highly desirable, essential or nutritionally advantageous carboxylic acid such as oleic, linoleic, conjugated linoleic, linolenic, eicosapentaenoic acids, or the like. Alternatively, the more readily cleaved residue may be a low molecular weight carboxylic acid (e.g., acetic, propionic, butyric acids), or a less absorbable acid (e.g., stearic or erucic acids), which would limit caloric delivery and provide additional ability to control functionality. Another advantage offered within the scope of the present invention is the ability to enable the construction of novel molecules whose molecular weights, melting ranges, texture, and viscosity properties may be engineered so as to fall within the same desirable ranges found for natural fats and oils and thus emulate the properties and the functionality of natural fats and oils used in food products.

Among the carboxy/carboxylate esters preferred for many applications are those with melting points below about 98° F. because these materials melt completely in the mouth, providing the organoleptic sensation of natural fats and oils. For some products, relatively sharp melting points, e.g., in the range of from about 90 to 98 F, are desired because they provide a cooling sensation and meltdown equivalent to high quality, solid natural fats. Preferred partially digestible carboxy/carboxylate disubstituted ester fat mimetics of this invention deliver less than 9 kcal/gram, more narrowly less than 5 kcal/gram, and even more narrowly, less than 3 kcal/gram upon being metabolized.

Carboxy/carboxylate disubstituted esters may be incorporated either alone, or in combination with another fat and/or fat mimetic, into any food composition comprising fat and nonfat (food) ingredients, or used in conjunction with any edible material. Other fat mimetics include any heretofore suggested edible fat replacements, including, but not limited to, sugar esters, neoalkyl esters, polyglycerol esters, malonate esters, propoxylated glycerols, retrofats, silicone oils/siloxanes, other carboxy/carboxylates, and the like.

The term "edible material" is broad and includes anything edible, whether or not intended for nutrition, e.g., it can be an additive such as an antioxidant for fats or oils, an antispatter agent, a texture modifier such as a plasticizer for chewing gum, or other minor functional ingredient such as a carrier or diluent for use in flavorings, pharmaceuticals, and the like. Thus, chewing gum, flavored coatings, oils and fats intended only for frying, and the like are included. In these, all or a portion of the usual fat is replaced by a compound of the invention.

Representative of edible fat-containing materials which can contain, in addition to other food ingredients, the fat mimetic compounds of the invention in full or partial replacement of natural fat are: frozen deserts, e.g., ice cream, frozen novelties, ices, milk shakes, and sherbert; puddings and pie fillings; margarine substitutes or blends; flavored bread or biscuit spreads; mayonnaise; salad dressings, both emulsified and non-emulsified; filled dairy products such as filled cream or filled milk; dairy or non-dairy cheese spreads; coffee lighteners, liquid and dried; flavored dips; frying fats and oils; reformed and comminuted meats; meat substitutes or extenders; pet foods; whipped toppings; compound coatings; frostings and fillings; cocoa butter replacements or blends; candy, especially fatty candies such as containing peanut butter or chocolate; chewing gum; bakery products, e.g., cakes, breads, rolls, pastries, cookies, biscuits, savory crackers; mixes or ingredient pre-mixes for any of these; as well as flavor, nutrient, drug or functional additive delivery systems. Most of the food compositions prepared using the fat mimetic compounds of this invention contain no diphenylamine.

The following is a list of representative, but nonlimiting, examples of carboxy/carboxylate disubstituted esters of this invention:

(A) Acylated hydroxycarboxylic acid esters of the formula

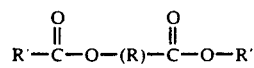

wherein
R is an aliphatic group having 2 to 20 carbons, and
R' is an aliphatic group having 1 to 30 carbon atoms,
the various R' groups being the same or different.
Examples of this type of carboxy/carboxylate fat mimetic include

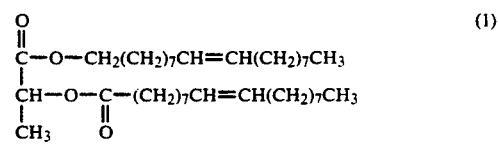 (1)

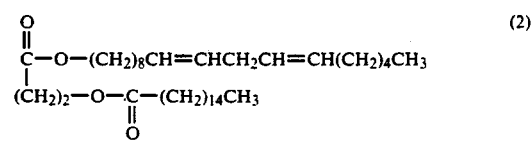 (2)

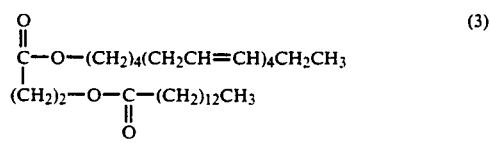 (3)

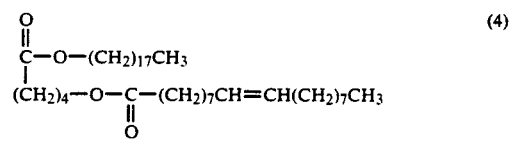 (4)

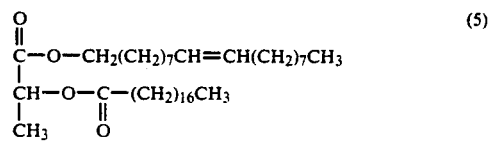 (5)

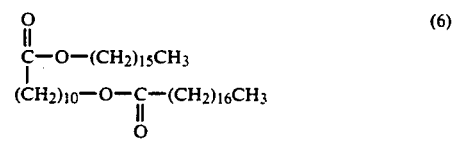 (6)

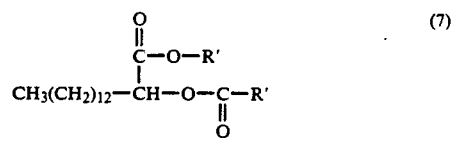 (7)

where the R' groups are derived from corn oil

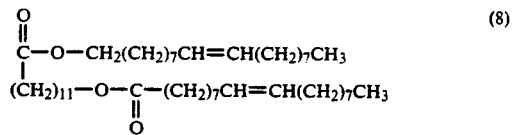 (8)

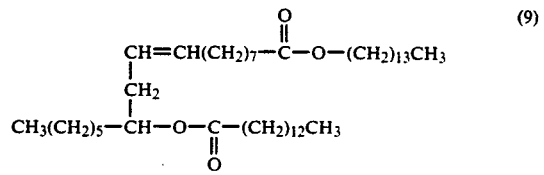 (9)

-continued

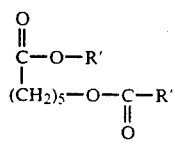

(10)

where R' is derived from sunflower oil (B) Acylated oligomeric hydroxycarboxylic acid esters of the formula

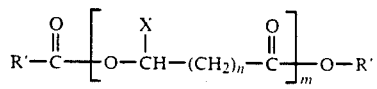

where
M = 2 to 20,
N = 0 to 12,
X = H, or an alkyl group having 1 to 16 carbon atoms, and
R' is an aliphatic group having 1 to 30 carbon atoms, the various R' groups being the same or different.

These include lactic acid oligomers having X=CH$_3$, M=2 to 10, and N=0.

Examples of this type of carboxy/carboxylate fat mimetic include:

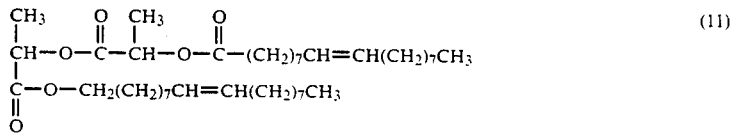
(11)

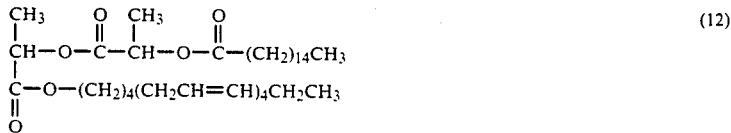
(12)

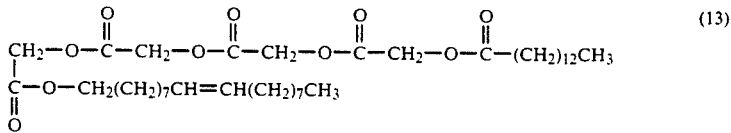
(13)

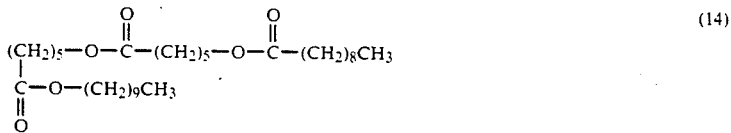
(14)

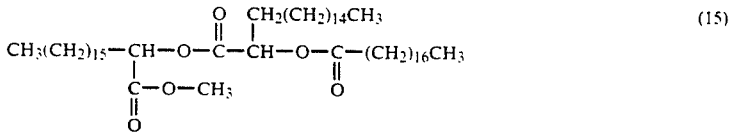
(15)

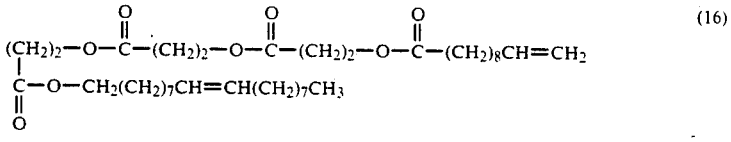
(16)

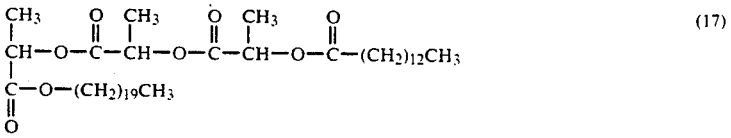
(17)

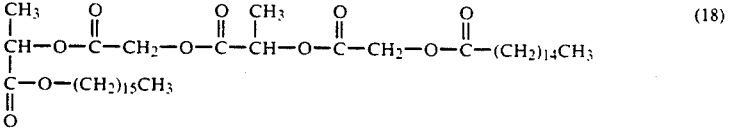
(18)

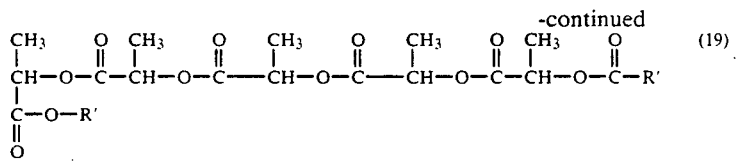

(19)

where the R' groups are derived from safflower oil

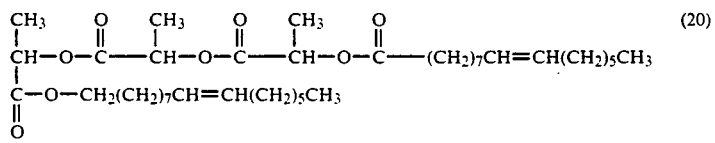

(20)

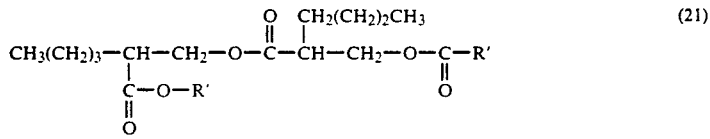

(21)

where the R' groups are derived from soybean oil

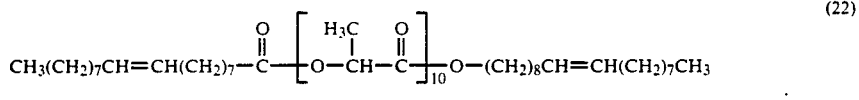

(22)

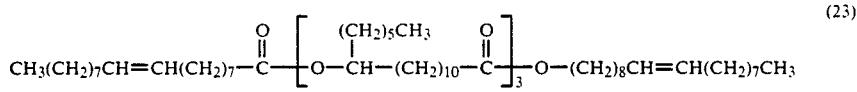

(23)

EXAMPLES

The following examples are presented to further illustrate and explain the present invention and should not be taken as limiting in any regard. Unless otherwise indicated, all parts and percentages are by weight, and are based on the weight at the particular stage of the processing being described.

Example 1

Oleoyl lactic oleate, a carboxy/carboxylate fat mimetic illustrated as structure (1) above, is prepared in this example.

A 50-ml round bottomed flask equipped with a magnetic stirrer and a micro vacuum distillation apparatus is charged with 3 g lactic acid, 9 g oleyl alcohol, and 1 g amberlyst ion exchange resin. Heat is applied by means of a mantle to reach and maintain a temperature of 120° C. for 4 hours while a vacuum of 100 Torr is applied. The contents of the flask are then cooled, diluted with hexane, filtered through #4 Whatman paper (to remove amberlyst), and concentrated on a rotary evaporator.

The water distillate is discarded, and the oily product is transferred to a 250-ml round bottom flask equipped with a magnetic stirrer. To this is added 50 ml pyridine. The flask is attached to a reflux condenser and emerged in an ice bath. Oleoyl chloride (29.6 g) is added through an addition funnel dropwise with constant stirring. After addition is complete, the flask is removed from the ice bath, and heat is applied to bring the sample to reflux. After refluxing one hour, the mixture is cooled to ambient temperature and diluted with hexane. The flask contents are transferred to a separatory funnel and washed three times with 50 ml 5% HCl solution, then once with 50 ml distilled water. The sample is dried over magnesium sulfate, filtered through #4 Whatman paper, and concentrated on a rotary evaporator. The product is then flash-chromatographed through silica gel using heptane as a solvent. It is then collected, concentrated on a rotary evaporator, and deodorized.

Example 2

Oleoyl lactyl lactic oleate, a carboxy/carboxylate diglyceride mimetic illustrated as structure (11) above, is prepared in a three-step reaction in this example.

Step 1: Preparation of Lactyl Lactate. A 250-ml flask equipped with a magnetic stirrer and distillation apparatus is charged with 150 ml of lactic acid. The flask is heated to 120° C. without a vacuum. After 10 hours, the flask is cooled to ambient temperature, and the water distillate is discarded.

Step 2: Esterification of Lactyl Lactate. Lactyl lactate (50 grams of the intermediate prepared above) is transferred to a 500-ml two-neck round bottom flask and 85 g oleoyl alcohol and 5 g amberlyst (XN 1010 ion exchange resin) are added. The flask is attached to a vacuum distillation apparatus and heated with a mantle to a temperature of 120° C. under a 100 Torr vacuum for 4 hours. The flask is cooled to ambient temperature, diluted with 500 ml hexane, filtered through #4 Whatman paper (to remove amberlyst), and concentrated on a rotary evaporator.

Step 3: Acylation of Esterified Lactyl Lactate. The product from step 2 is then transferred to a 1000-ml, two-neck flask equipped with a stirrer bar, and 150 ml pyridine are added. A reflux condenser is attached, and the flask is submerged in an ice bath. Oleoyl chloride (95 grams, 105 ml) is added dropwise through an addition funnel. After the oleoyl chloride has been added, the mixture is heated with a heating mantle to reflux. After refluxing one hour, the flask is cooled to ambient temperature and diluted with hexane. The product is transferred to a separatory funnel and washed with 3 100 ml aliquots of 5% HCl, followed by one 100 ml water wash. The product is then dried over magnesium sulfate, filtered through #4 paper, and concentrated. The product is finally purified by flash-chromatography through silica gel (using heptane as a solvent), collection, concentration, and deodorization.

Example 3

Another carboxy/carboxylate fat mimetic of this invention, an oligomeric lactyl lactate acylated with oleic acid and esterified with oleyl alcohol (depicted in structure (22) above), is prepared in this example.

A 2000-ml round bottom flask equipped with a magnetic stirrer, heating mantle, and vacuum adapter is charged with 995 g lactic acid and heated to a temperature of 120° C. for 16 hours under a vacuum of 100 Torr. The flask is then cooled to ambient temperature and the water distillate is discarded.

The viscous, clear yellow product (392 g) is transferred to a second 2000-ml flask equipped with a mechanical stirrer and vacuum adapter. To this flask is added 300 g oleyl alcohol. The flask is heated with a mantle to a temperature of 150° C. under a vacuum of 100 Torr for 16 hours. After cooling to ambient temperature, the water distillate is discarded and excess oleyl alcohol is removed by falling film distillation.

The remaining product is transferred to a two-neck 2000-ml round bottom flask equipped with a mechanical stirrer and vacuum adapter. To this is added 300 g of oleoyl chloride. A potassium hydroxide trap is installed between the flask and vacuum pump to capture the evolved HCl. The flask is heated using a heating mantle to a temperature of 120° C. for 5 hours. The resulting product is flash chromatographed using heptane as a solvent, and deodorized.

Example 4

Another fat mimetic of this invention, 12- oleoyloxydodecanoic oleate (depicted in structure (8) above), is prepared in this example.

A 250-ml round bottom flask equipped with a magnetic stirrer and vacuum adapter is charged with 50 g of 12-hydroxydodecanoic acid and 65 g of oleyl alcohol. The flask is heated to a temperature of 150° C. under a 100 Torr vacuum for 16 hours. The flask is then cooled to ambient temperature, and excess oleyl alcohol removed by falling film distillation.

The remaining product is transferred to a 500-ml round bottom flask equipped with a magnetic stirrer and vacuum adapter. To this is added 75 g of oleoyl chloride. A potassium hydroxide trap is installed between the flask and the vacuum pump to capture the evolved HCl gas. The flask is heated with a mantle to a temperature of 120° C. under 100 Torr vacuum for 5 hours. The remaining product is flash chromatographed through silica gel using heptane as a solvent. It is collected, concentrated on a rotary evaporator, and deodorized.

Example 5

This example outlines a procedure for estimating the in vitro digestibility of the diglyceride mimetics of this invention using pancreatic lipase.

Preparation of Reagents and Materials:

1. Buffer: A pH 7.1 phosphate buffer is prepared by dissolving 6.8 g. $KH_2PO_4$ in 1 L. of millipore filtered water (to yield 0.05 M phosphate). Fifty mg. $Ca(NO_3)_2$ and 5.0 g. cholic acid (Na salt, an ox bile isolate from Sigma) are added to give 300 microM $Ca^{++}$ and 0.5 % cholic acid in 0.05 M phosphate. The pH is adjusted to approximately 7.1 with solid NaOH. Several drops of Baker "Resi-analyzed" toluene are added to prevent bacterial growth during storage at 3–5° C.

2. Lipase: About 15 mg./mL commercial porcine pancreatic lipase from U.S. Biochemical Corporation is dissolved in buffer.

3. Substrates and Standards: A 1.0 mL volumetric flask is charged with an amount of lipid substrate (test substance or standard) calculated to give a concentration of 200 nanomoles per microliter in Baker "Resi-analyzed" toluene. (The proper concentration may be approximated by doubling the molecular weight of the lipid in question, dividing by 10, and diluting to the mark on the volumetric flask; this yields about 200 nanomoles per microliter.) This preparation affords the substrate to be used in the hydrolysis reactions.

Fatty acids and glyceride standards from Nu Chek or Sigma are prepared for elution on TLC plates (prewashed with 1:1 chloroform/methanol) by diluting the substrate solution with 10:1 toluene (1 part substrate plus 9 parts toluene) in septum vials.

Procedure:

In a 25 mL Erlenmeyer, emulsify 20 mL buffer and 40 microliters of substrate using an ultrasonic disrupter at a microtip maximum setting for approximately 10 seconds. This results in a 0.4 microliter/milliliter emulsion. Place in a 37° C. water bath and stir vigorously. After temperature equilibration, add 40 microliters of enzyme solution and start timing. Remove 5.0 mL aliquots at convenient time intervals for analysis. To establish a standard curve for triolein, aliquots are taken at 10, 20, 30 and 40 minutes. A zero time control should be run for all test compounds.

Add the aliquot to a 15 mL glass centrifuge tube containing a drop of concentrated HCl. Add approximately 3 mL of a 2:1 mixture of $CHCl_3:CH_3OH$ and shake vigorously. Centrifuge at approximately 5000 rpm for 5 minutes and transfer the bottom layer with a Pasteur pipet to a 5 mL septum vial. Repeat the extraction step once and combine the two bottom layers. Evaporate the solvent in nitrogen gas. After about half of the solvent is removed, add an equivalent volume absolute ethanol and continue evaporation in a nitrogen stream until dryness is achieved. Samples may be warmed with a heat gun to facilitate drying.

When the samples are dry, add exactly 200 microliters of toluene containing 10% DMSO, cap tightly, and spot TLC plate with 2.0 microliters per channel. (If 100% extraction efficiency of a zero time control, this amounts to 20 nanomoles of substrate spotted on the plate.) Develop with a suitable solvent system, for example, hexane: ethyl ether: acetic acid in a ratio of 60:40:1. After 15 cm elution, dry plate with a heat gun and determine amounts of starting substrate and products of hydrolysis by scanning 10 to 20 nanomoles per channel at a wavelength of 190 nm using the CAMAG TLC Scanner II densitometer equipped with a Spectra Physics 4270 integrator and comparing with controls run at the same time.

Results:

Using this procedure and enzyme system, triolein is substantially hydrolyzed in ten minutes. Under the same conditions, the fat mimetic of Example 2 is not hydrolyzed in 3 hours.

Example 6

Puff Pastry Shortening. A puff pastry shortening may be prepared by homogenizing

| Ingredient | parts |
| --- | --- |
| Fat Mimetic of Example 2 | 68.0 |
| Fat Mimetic of Example 4 | 22.0 |
| Soybean Lecithin | 0.1 |
| Mono- and Diglycerides (0 IV) | 0.2 |
| with Water | 8.2 |
| Salt | 1.5 |

Example 7

Frying Oil. A frying oil may be prepared by adding 1 ppm polydimethylsiloxane to the fat mimetic of Example 1.

Example 8

Potato Chips. Whole peeled potatoes may be sliced, washed in water, and fried in an equal parts mixture of peanut oil and fat mimetic of Example 2 at 375. F to desired color. The excess oil is shaken off and the chips ar salted.

Example 9

Imitation Sour Cream. An imitation sour cream may be prepared by adding

|  | parts |
| --- | --- |
| Water | 75.8 |
| to Modified Starch | 2.0 |
| Avicel | 1.0 |
| Distilled Monoglyceride | 0.7 |
| and Polysorbate 6 | 0.3 | and mixing three minutes. To this is added

| Fat Mimetic of Example 3 | 16.5 |
| --- | --- |
| Condensed Skim Milk | 3.5 | and the mixture mixed three minutes. cooked to 195° F., and held five minutes. This may then be cooled to 60° F., and

| Flavors and Acids | 0.2 |
| --- | --- | added, followed by filling in the usual process.

Example 10

Dijon Mustard. A Dijon-style mustard may be prepared by combining

| Ingredient | parts |
| --- | --- |
| Dry White Wine | 66.1 |
| with Water | 5.0 | and bringing to a boil. To this aqueous phase is added

| Ground, Defatted Yellow Mustard Seed | 12.4 |
| --- | --- |
| Fat Mimetic of Example 1 | 6.1 |
| Honey | 6.6 |
| Onion Powder | 2.0 |

-continued

| Salt | 1.3 |
| --- | --- |
| Garlic Powder | 0.3 |
| Mustard Oleo Resin | 0.2 |

The mixture is well blended, pasteurized and packaged.

Example 11

Sandwich Cookies. A basecake may be prepared by combining

| Ingredient | parts |
| --- | --- |
| Flour | 48.0 |
| High Fructose Corn Syrup | 12.0 |
| Sugar (6X) | 10.0 |
| Example 1 Fat Mimetic | 10.0 |
| Dutched Cocoa | 5.0 |
| Corn Syrup (42 D.E.) | 3.0 |
| Dextrose | 2.0 |
| Frozen Whole Eggs | 2.0 |
| Salt | 0.3 |
| Sodium Bicarbonate | 0.2 |
| Lecithin | 0.2 |
| Vanilla | 0.2 |
| Ammonium Bicarbonate | 0.1 |
| Water | 7.0 | mixing well, rotary molding, baking and cooling. A filler may be prepared by heating slightly

| Example 4 Fat Mimetic | 37.0 |
| --- | --- | and adding

| Sugar 10X | 62.7 |
| --- | --- |
| Vanillin | 0.3 |

Cool filler to 78° F. and sandwich between base cakes in a ratio of 1 to 3.

Example 12

Peanut Butter. Peanut butter may be prepared by mixing

| Ingredient | parts |
| --- | --- |
| Example 4 Fat Mimetic | 35.0 |
| with Peanut Flavor | 2.0. |
| Then Corn Syrup Solids | 12.0 |
| Salt | 1.0 |
| High Fructose Corn Syrup | 10.0 | are added while agitating. When well blended, add

| Defatted Peanut Flour | 40.0 |
| --- | --- | mix and package.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims.

What is claimed is:

1. An edible composition comprising a fat mimetic of the formula:

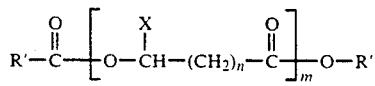

where
m = 2 to 20,
n = 0 to 12,
X = H, or an alkyl group having 1 to 16 carbon atoms, and
R' is an aliphatic group having 1 to 30 carbon atoms, the various R' groups being the same or different and at least one other edible ingredient.

2. A composition according to claim 1 wherein m = 3 to 10.

3. A composition according to claim 1 wherein said edible composition is a food composition.

4. An edible composition containing a fat ingredient wherein at least a portion of said fat ingredient is replaced by a fat mimetic of the formula

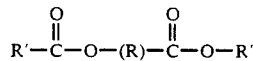

wherein
R is an aliphatic group having 2 to 20, carbons, and
R' is an aliphatic group having 10 to 20 carbon atoms, the various R' groups being the same or different and at least one other edible ingredient.

5. A composition according to claim 1 comprising a compound selected from the group consisting of

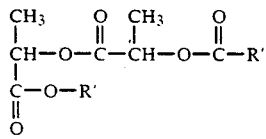

and compounds of the formula

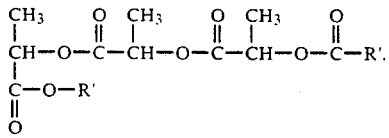

6. A composition according to claim 5 wherein said fat mimetic has the formula

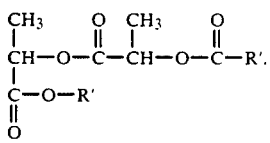

7. A composition according to claims 1, 5 or 6 wherein the R' groups contain 4 to 23 carbon atoms.

8. A composition according to claim 7 wherein the R' groups contain 14 to 18 carbon atoms.

9. A composition according to claims 1, 5, or 6 wherein the R' groups are derived from fatty acids selected from the group consisting of acetic, propionic, butyric, caproic, caprylic, pelargonic, capric, undecanoic, lauric, myristic, palmitic, stearic, arachidic, behenic, lignoceric, cerotic, montanic, melissic, palmitoleic, oleic, vaccenic, linoleic, linolenic, eleostearic, arachidonic, erucic, brassidic, nervonic, eicosapentaenoic, docosatetraenoic, docosapentaenoic, and docosahexaenoic acids, their alcohol counterparts, and mixtures thereof.

10. A composition according to claims 1, 4 or 5 wherein the R' groups are derived from mixtures obtained from the hydrolysis of unhydrogenated, partially hydrogenated, or fully hydrogenated oils selected from the group consisting of soybean, safflower, sunflower, sesame, peanut, corn, olive, rice bran, canola, babassu nut, coconut, palm, palm kernel, lupin, nasturtium seed, mustard seed, cottonseed, low erucic rapeseed, milk butterfat and marine oils, and fractions thereof.

11. A method for preparing an edible composition having a digestible fat component comprising incorporating into said composition a compound of the formula

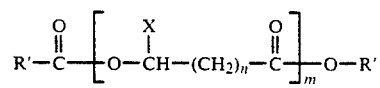

where
m = 2 to 20,
n = 0 to 12,
X = H, or an alkyl group having 1 to 16 carbon atoms, and
R' is an aliphatic group having 1 to 30 carbon atoms, the various R, groups being the same or different in full or partial replacement of said digestible fat component.

12. A method for reducing the available calories in a food composition having an edible fat component, which method comprises replacing at least a portion of the edible fat with a compound of the formula

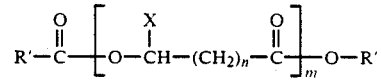

where
m = 1 to 20,
n = 0 to 12,
X = H, or an alkyl group having 1 to 16 carbon atoms, and
R' is an aliphatic group having 1 to 30 carbon atoms, the various R' groups being the same or different.

13. A method according to claims 11 or 12 wherein R' has 3 to 24 carbon atoms.

14. A method according to claims 11 or 12 wherein the R' groups are derived from fatty acids selected from the group consisting of acetic, propionic, butyric, caproic, caprylic, pelargonic, capric, undecanoic, lauric, myristic, palmitic, stearic, arachidic, behenic, lignoceric, cerotic, montanic, melissic, palmitoleic, oleic, vaccenic, linoleic, linolenic, eleostearic, arachidonic, erucic, brassidic, nervonic, eicosapentaenoic, docosatetraenoic, docosapentaenoic, and docosahexaenoic acids, their alcohol counterparts, and mixtures thereof.

15. A method according to claims 11 or 12 wherein the R' groups are derived from mixtures obtained from the hydrolysis of unhydrogenated, partially hydrogenated, or fully hydrogenated oils selected from the group consisting of soybean, safflower, sunflower, sesame, peanut, corn, olive, rice bran, canola, babassu nut, coconut, palm, palm kernel, lupin, nasturtium seed, mustard seed, cottonseed, low erucic rapeseed, milk butterfat and marine oils, and fractions thereof.

16. A method according to claims 11 or 12 wherein X is $CH_3$, $M = 2$ to 10, and $N = 0$.

17. A method according to claims 11 or 12 wherein said compound delivers less than 5 kcal/gram upon being metabolized.

18. A method according to claim 17 wherein said compound delivers less than 3 kcal/gram upon being metabolized.

19. A method for preparing a reduced calorie food composition which comprises formulating said composition with an edible fat memetic comprising a $C_1$ to $C_{30}$ fatty acid acylated, $C_1$ to $C_{30}$ fatty alcohol esterified lactic acid oligomer having 2 to 20 lactic acidowits.

20. A reduced calorie bakery product made according to the method of claim 19 and further comprising flour.

* * * * *